United States Patent [19]
Vennes et al.

[11] Patent Number: 5,620,408
[45] Date of Patent: Apr. 15, 1997

[54] ENDOSCOPIC OVER-TUBE

[76] Inventors: Jack A. Vennes, 18905 12th Ave. North, Plymouth, Minn. 55447; Jeff M. Rank, 2249 Fairmont Ave., St. Paul, Minn. 55105

[21] Appl. No.: 421,986

[22] Filed: Apr. 14, 1995

[51] Int. Cl.$^6$ ............................................. A61B 1/04
[52] U.S. Cl. ..................... 600/114; 600/115; 600/120; 600/121; 128/200.26; 128/201.14
[58] Field of Search ........................... 600/114, 115, 600/120, 121, 139, 207, 206, 194, 237, 238; 606/108; 604/96; 128/200.26, 207.14, 207.17, 911, 912, DIG. 26, 898; 433/93, 143

[56] References Cited

U.S. PATENT DOCUMENTS 4,688,568  8/1987  Frass et al. .
4,974,580  12/1990 Anapliotis .
5,088,979  2/1992  Filipi et al. .
5,127,393  7/1992  McFarlin et al. .

*Primary Examiner*—Richard J. Apley
*Assistant Examiner*—Beverly M. Flanagan
*Attorney, Agent, or Firm*—Merchant, Gould, Smith, Edell, Welter & Schmidt, P.A.

[57] ABSTRACT

The present invention is an endoscopic over-tube for receiving and guiding medical instrumentation into the upper alimentary canal of a patient. The endoscopic over-tube has a bite block for insertion and retention in the mouth of the patient. The endoscopic over-tube also has a flexible protective sheath engaging the bite block and adapted for insertion into the upper alimentary canal of the patient. The sheath includes a stiffened region that insulates the posterior wall of the patient's pharynx from medical instrumentation as the medical instrumentation is intubated through the sheath and into the patient's alimentary canal.

19 Claims, 2 Drawing Sheets

ENDOSCOPIC OVER-TUBE

FIELD OF THE INVENTION

The present invention relates generally to flexible tubes for guiding medical instrumentation. Specifically, the invention relates to tubes suitable for guiding medical instrumentation through the alimentary canal, the tubes having stiffened regions that align with the posterior wall of the pharynx, such that upon passage of medical instrumentation through the tubes, gag reflexes are prevented.

BACKGROUND OF THE INVENTION

Endoscopy of the upper gastrointestinal tract typically involves passing one or more medical instruments through the alimentary canal. For example, endoscopes having different sizes may be sequentially intubated through the upper alimentary canal which includes the mouth, pharynx, esophagus, stomach and upper small intestine. Furthermore, prior to endoscopy, it is often necessary to evacuate the stomach of contents such as blood with an evacuation tube such as a lavage tube.

During conventional intubation such as endoscopy or evacuation of the upper alimentary canal, medical instrumentation is advanced from the patient's mouth into the patient's upper pharynx. Each time a medical instrument is advanced from the patient's mouth into the patient's pharynx, the medical instrument contacts the posterior wall of the pharynx, commonly known in the art as the "gag zone". This contact is typically unavoidable because the cavity of the mouth and the cavity of the pharynx are aligned at approximately right angles to one another, thereby forcing the medical instrumentation to be advanced through a tight curve. When medical instrumentation contacts the posterior wall of the pharynx, the gag zone is irritated, typically stimulating a gag reflex in the patient.

Gag reflexes are undesirable as the patient commonly experiences physical discomfort, may suffer respiratory damage or pneumonia due to the aspiration of blood and digestive fluids, may suffer damage to the alimentary canal as a result of the medical instrumentation moving therein, and may cause the medical instrumentation within the alimentary canal to move, thereby interfering with the successful completion of the medical procedure.

Conventionally, gag reflexes during intubation of the alimentary canal have been prevented by the combination of intravenous sedation prior to intubation along with the application of local anesthetics directly to the alimentary canal. The local anesthetics are applied to the alimentary canal as either throat sprays or as coatings applied to the medical instrumentation. The above-described combination numbs and relaxes the pharynx of the patient, thereby preventing a gag reflex.

A major draw back to the conventional method of endoscopy is that patients may react negatively to the intravenous sedatives. These reactions to the intravenous sedatives can vary greatly from patient to patient. Common reactions to intravenous sedatives include respiratory failure and heart rhythm disturbances. Additionally, a sedated patient is much more likely to aspirate blood or other stomach contents. Furthermore, the use of intravenous sedatives significantly increases post endoscopy recovery times, thereby increasing the cost of the procedure.

SUMMARY OF THE INVENTION

The present invention improves on the prior art by providing an intubation device that minimizes or eliminates any gag reflexes during intubation of the alimentary canal without requiring intravenous sedation of the patient.

The present invention is an endoscopic over-tube for receiving and guiding medical instrumentation into the upper alimentary canal of a patient. The endoscopic over-tube includes a bite block for insertion and retention in the mouth of the patient, and a flexible protective sheath engaging the bite block and adapted for insertion into the upper alimentary canal of the patient. The sheath includes a somewhat stiffened region positioned at a location along the length of the sheath such that when the sheath is inserted into the patient's alimentary canal, the stiffened region aligns with the posterior wall of the pharynx. The stiffened region insulates the posterior wall of the patient's pharynx from medical instrumentation as the medical instrumentation is advanced through the sheath and into the patient's alimentary canal.

Another aspect of the present invention involves an endoscopic over-tube adapted for use in patients experiencing bleeding of the gastrointestinal tract. The over-tube includes an inflatable cuff for sealing the patient's esophagus during intubation and endoscopic examination. By sealing the esophagus, the potential for aspiration of blood and other stomach contents is minimized.

The present invention also discloses a method for performing an endoscopy of the alimentary canal of a patient. The method includes providing a flexible protective sheath defining a longitudinal bore for receiving an endoscope and having a stiffened region. The method also includes advancing the sheath through the upper alimentary canal of the patient such that the stiffened region of the sheath is aligned with the posterior wall of the patient's pharynx. The method further includes advancing an endoscope through the sheath and into the alimentary canal of the patient. The stiffened region of the sheath prevents a gag reflex during endoscopy.

BRIEF DESCRIPTION OF THE DRAWINGS

The accompanying drawings, which are incorporated in and constitute part of this specification, illustrate several embodiments of the invention and together with the description, serve to explain the principles of the invention. A brief description of the drawings is as follows.

DETAILED DESCRIPTION OF THE PREFERRED EMBODIMENT

Figure 1:
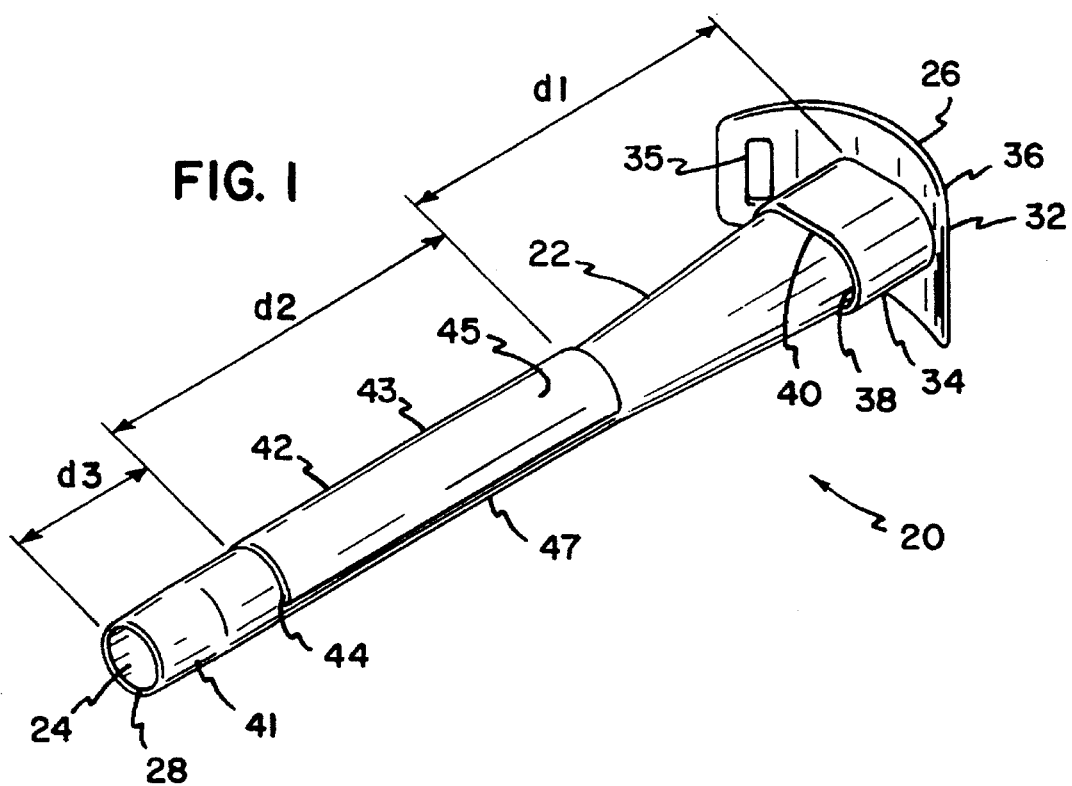
FIG. 1 is a perspective view of an embodiment of an endoscopic over-tube of the present invention.

Reference will now be made in detail to exemplary embodiments of the present invention which are illustrated in the accompanying drawings. Wherever possible, the same reference numerals will be used throughout the drawings to refer to the same or like parts.

Referring now to FIG. 1, there is illustrated a endoscopic over-tube 20 which is an embodiment of the present invention. The endoscopic over-tube 20 has a generally tubular flexible protective sheath 22 having a first end 26 and a second end 28 The sheath 22 is suitable for insertion into the upper alimentary canal of a patient and defines a generally cylindrical longitudinal bore 24 throughout its length. The longitudinal bore 24 has a diameter generally in the range of 14–16 millimeters. The wall thickness of the sheath 22 is generally in the range of 1–2 millimeters while the length of the sheath 22 is in the range of 22–24 centimeters. Preferably, the sheath is constructed of a soft flexible material such as polyurethane or polyvinyl chloride. However, any material having comparable physical characteristics may be used.

The first end 26 of the sheath 22 is connected to a conventional mouth-piece 32 typically formed from medical grade plastic. The mouth-piece 32 has a bite-block portion 34 integral with a flange portion 36. The bite-block portion 34 is adapted for insertion in the patient's mouth to prevent the patient from biting down on the sheath 22. The bite-block portion 34 has an inner surface 38 that defines a hole 40 for receiving and engaging the sheath 22. The sheath 22 tapers outwardly adjacent the first end 26 to coincide with the dimensions of the hole 40 within the bite-block portion 34.

The first end 26 of the sheath 22 is preferably attached to the inner surface 38 of the hole 40 in the bite block portion 34 by conventional fastening techniques such as vulcanization, use of adhesives, hot pressing, etc. However, the sheath 22 may slidingly engage the inner surface 38 of the bite-block portion 34.

The flange portion 36 of the mouth-piece 32 extends radially outward from the bite-block portion 34 to prevent the patient from swallowing the mouth piece 32. The flange portion 36 also defines a pair of holes 35 for connecting an elastic strap (not shown) to the mouth-piece 32. The elastic strap (not shown) keeps the mouth-piece 32 within the patient's mouth during endoscopy.

Figure 2:
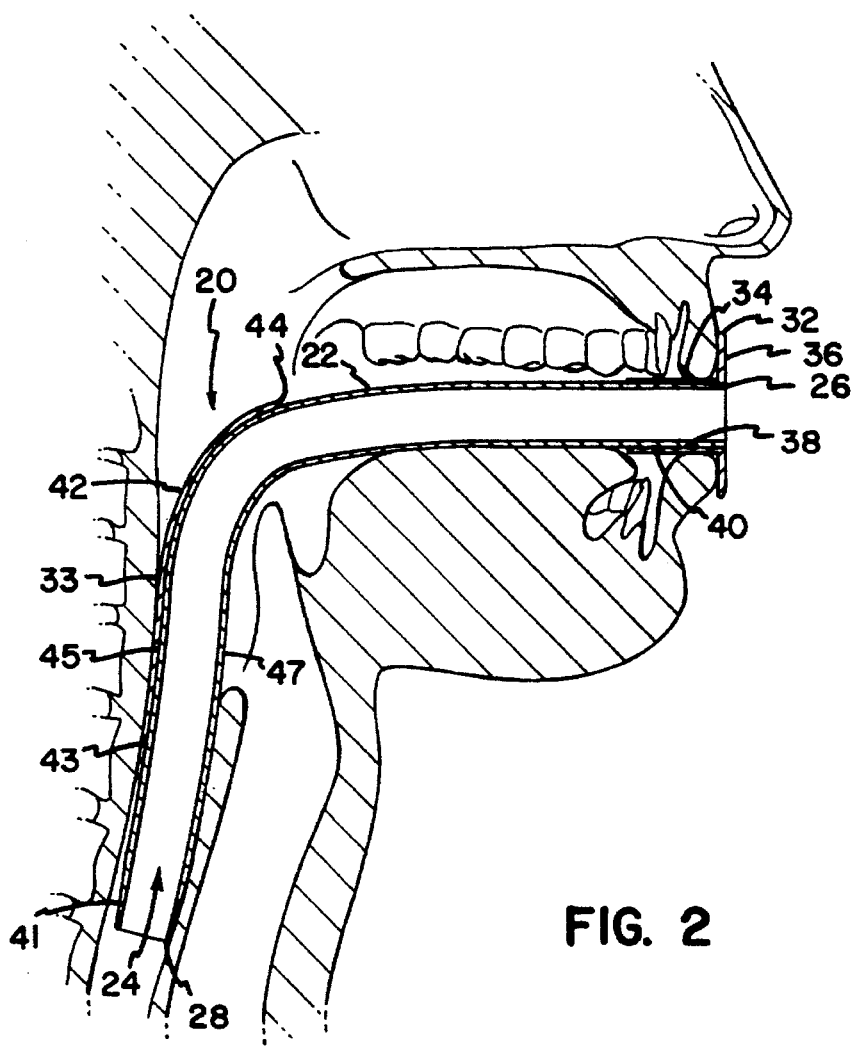
FIG. 2 is a sectional view of the endoscopic over-tube of FIG. 1 in the alimentary canal of a patient.

The second end 28 of the sheath 22 is adapted for insertion into the upper alimentary canal of the patient. Because the second end 28 of the sheath 22 is soft and flexible, the sheath 22 can be advanced along the posterior wall of the pharynx and into the esophagus of the patient without irritating the gag zone 33 as shown in FIG. 2. Additionally, the sheath 22 may include a tapered portion 41 positioned adjacent to the second end 28. The wall thickness of the sheath 22 is gradually decreased along the tapered portion 41 such that the wall is thinnest at the second end 28 of the sheath 22. The reduced wall thickness of the tapered portion 41 makes the second end 28 extremely soft and flexible thereby facilitating advancement of the sheath 22 through the alimentary canal.

A stiffened region 42 is intermediate the first end 26 and the second end 28 of the sheath 22. The beginning of the stiffened region 42 is located a first distance $d_1$ from the first end 26 of the sheath 22. The first distance $d_1$ generally equals approximately 10 centimeters for an average adult patient. However, when adapted for pediatric use, the distance $d_1$ may be varied to complement to physical dimensions of the pediatric patient's upper alimentary canal.

From the position defined by $d_1$, the stiffened region 42 extends a second distance $d_2$ along the sheath 22 towards the second end 28. The second distance $d_2$ generally equals approximately 10 centimeters for an average patient. However, when the endoscopic over-tube 20 is adapted for pediatric use, the distance $d_2$ may be varied to correspond to the physical dimensions of the pediatric patient's upper alimentary canal.

The end of the stiffened region 42 is located a third distance $d_3$ from the second end 28 of the sheath 22. This third distance $d_3$ is preferably equal to approximately 2–4 centimeters. However, depending on the specific procedure in which the endoscopic over-tube 20 is being used, this third distance $d_3$ may be outside the above described range.

The stiffened region 42 is preferably constructed by wrapping a reinforcing layer 44 of flexible material such as polyurethane or polyvinyl chloride around the outside of the sheath 22 thereby creating a thickened portion 43. The layer 44 provides an increased stiffness and thickness along the portion of the sheath 22 designated by distance $d_2$. Preferably, the layer 44 has a thickness ranging from 1–2 millimeters. The layer 44 is affixed to the sheath 22 by conventional fastening techniques such as vulcanization, use of adhesives, hot pressing, etc.

It is preferred that the layer 44 extend along the portion of the sheath designated by distance $d_2$ and cover only a top half portion 45 of the sheath 22 (as shown in FIG. 1). However, the layer 34 can extend along the portion of the sheath designated by distance $d_2$ and cover the top half portion 45 and a bottom half portion 47 of the sheath 22 thereby completely encircling the sheath 22.

In an alternate embodiment of this invention, the layer 45 reinforcing the stiffened region 42 may be wrapped within the inside of the sheath 22 and affixed to the wall of the longitudinal bore 24. In another alternate embodiment, the sheath 22 may be extruded, formed or molded such that the portion of the sheath 22 designated by $d_2$ has a wall thickness greater than the wall thickness of the remainder of the sheath 22. This type of manufacturing process would eliminate the need for thickening the stiffened region 42 by affixing a reinforcing layer 45 to the sheath 22. In other alternate embodiments, the stiffened region 42 may be constructed by incorporating longitudinal ribbing within the wall of the portion of the sheath 22 designated by $d_2$.

In a further alternate embodiment, the stiffened region 42 may be created by constructing the portion of the sheath 22 designated by $d_2$ of a stiffer material than the remainder of the sheath 22. In this type of construction, the portion of the sheath 22 designated by $d_2$ will be attached to the more flexible portions of the sheath 22 designated by $d_1$ and $d_3$ by conventional fastening techniques such as vulcanization, use of adhesives, hot pressing, etc. This type of construction allows the sheath 22 to have a constant outer and inner diameter throughout its length.

Turning now to FIG. 2, when the above described endoscopic over-tube 20 is inserted into the patient's upper alimentary canal, the stiffened region 42 aligns along the gag zone 33 of the patient. The stiffened region 42 has a thickness stiffness which is sufficient to insulate and protect the gag zone 33 from irritation caused by medical instrumentation that is passed through the longitudinal bore 24 of the sheath 22. In this way, a gag reflex is prevented because the patient is unable to sense the medical instrumentation as it passes along the gag zone 33.

The stiffened region 42 insulates the gag zone 33 from irritation caused by medical instrumentation during advancement into the upper alimentary canal thereby preventing the patient from gagging. In this regard, it is important for the first distance $d_1$ of the sheath 22 to be approximately equal to the distance between the patient's lips and the posterior wall of the patient's upper pharynx so that the stiffened region 42 will be aligned with the gag zone 33 when the sheath is inserted into the upper alimentary canal. For most adults, the upper portion of the posterior wall of the pharynx is located approximately 10 centimeters from the lips. Therefore, by manufacturing the sheath 22 with the first distance $d_1$ equal to 10 centimeters, the endoscopic over-tube 20 would be suitable for use in most adults.

Similarly, it is important that the second distance $d_2$ of the sheath 22 be approximately equal to the length of the patient's gag zone 33 so that the stiffened region 42 will be aligned along the entire gag zone 33. For most adults, the length of the gag zone 33 is approximately 10 centimeters. Therefore, it is desireable to have an endoscopic over-tube having a sheath 22 with the second distance $d_2$ equal to 10 centimeters.

To perform an endoscopy or other intubation of the upper alimentary canal using the endoscopic over-tube 20, the patient's throat is first sprayed with a local anesthetic to numb the posterior wall of the pharynx and to minimize patient discomfort. The second end 28 of the sheath 22 is then inserted into the patient's mouth and advanced into the patient's upper pharynx. Because the tapered second end 28 of the sheath 22 is extremely soft and flexible, it is advanced through the curvature between the patient's mouth and the patient's upper pharynx without stimulating a gag response. As the second end 28 is advanced through the patient's pharynx, it leads the stiffened region 42 through the curve between the patient's mouth and the patient's upper pharynx thereby minimizing contact between the stiffened region 42 and the gag zone 33. This allows the stiffened region 42 to be moved through the gag zone 33 with a reduced likelihood of stimulating a gag response by the patient. The second end 28 of the sheath 22 is advanced through the patient's pharynx until it enters the patient's esophagus.

When the second end 28 of the sheath 22 is within the esophagus of the patient, the selectively stiffened region 42 is aligned along the patient's gag zone 33 and the bite block portion 34 of the mouth piece 32 is within the patient's mouth (as shown in FIG. 2). Medical instrumentation such as endoscopes, evacuation tubes, lavage tubes, etc., are then advanced through the longitudinal bore 24 of the sheath 22, to intubate the patient's alimentary canal. The stiffened region 42 has a thickness/stiffness which is sufficient to insulate and protect the gag zone 33 from irritation caused by the medical instrumentation that passes through the longitudinal bore 24 of the sheath 22. Gag reflexes are prevented because the patient is unable to sense the medical instrumentation during intubation through the gag zone 33. After the medical procedure is completed, the medical instrumentation is removed from the sheath 22 and the endoscopic over-tube 20 is removed from the alimentary canal of the patient.

In alternate embodiments of this invention, the sheath 22 may be manufactured having a curvature corresponding to the natural curvature of a patient's upper alimentary canal. This curvature would reduce the opportunity for kinking or creasing of the sheath 22 as it is inserted into a patient's upper alimentary canal.

Figure 3:
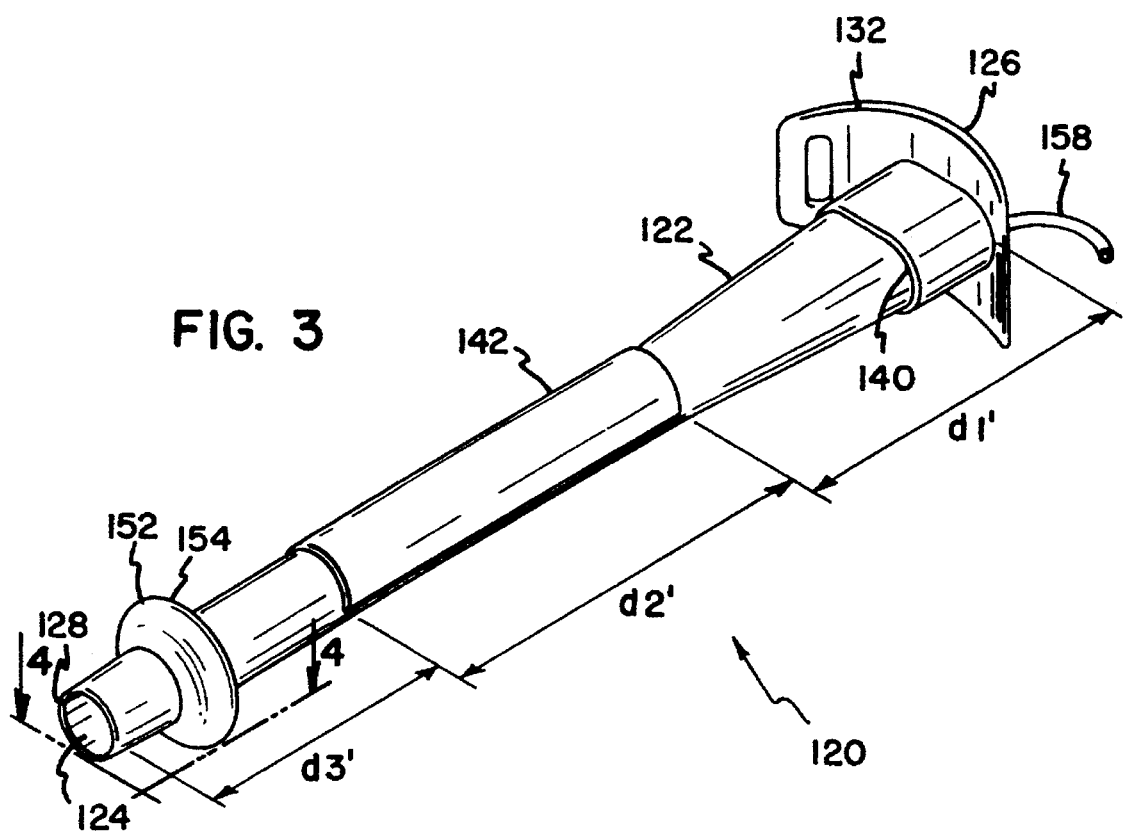
FIG. 3 is a perspective view of an alternative embodiment of an endoscopic over-tube of the present invention.
Figure 4:
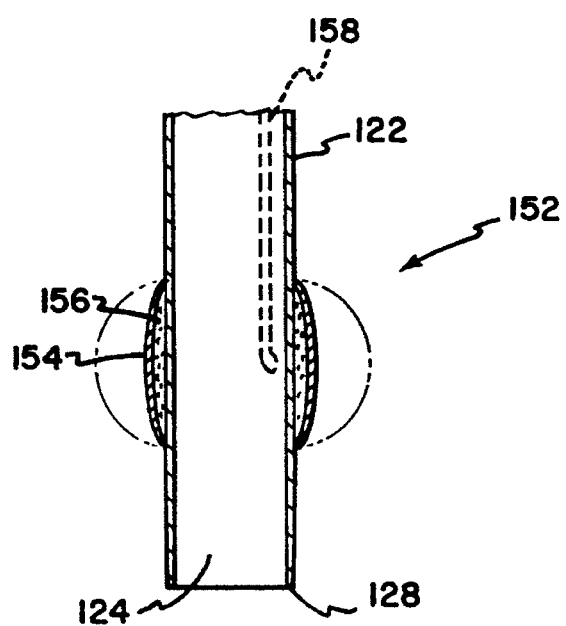
FIG. 4 is a cross-sectional view taken generally along section line 4—4 the endoscopic over-tube of FIG. 3

FIGS. 3 and 4 show a second embodiment of the endoscopic over-tube 120 of the present invention. The endoscopic over-tube 120 is suitable for use in assisting intubation of the upper alimentary canal of patients experiencing upper gastrointestinal hemorrhaging. For this type of patient, any gagging during intubation of the alimentary canal would cause the patient to regurgitate blood and other stomach contents. Regurgitation often causes the patient to aspirate blood and other stomach contents thereby causing severe complications such as difficulty in breathing, pneumonia or other damage to the lungs.

The endoscopic over-tube 120 has essentially the same construction as the endoscopic over-tube 20 (FIGS. 1 and 2) and includes similar elements such as a sheath 122 having a first end 126, a second end 128 and a longitudinal bore 124. The endoscopic over-tube 120 also has a mouth piece 132 and a stiffened region 142 intermediately positioned between the first end 126 and the second end 128. Furthermore, the endoscopic 120 over-tube has a first distance $d_{1'}$ and a second distance $d_{2'}$ which are essentially equal to the first distance $d_1$ and the second distance $d_2$ of the endoscopic over-tube 20.

The endoscopic over-tube 120 of the second embodiment differs from that shown above in that it has a longer third distance $d_{3'}$. In this regard, the third distance $d_{3'}$ is preferably within the range of 6–8 centimeters. The additional length provided by $d_{3'}$ allows the second end 128 of the endoscopic over-tube 120 to extend further into the esophagus of the patient than the second end 28 of the endoscopic over-tube 20 (FIGS. 1 and 2).

Another difference between the two embodiments is that endoscopic over-tube 120 has a structure for sealing the esophagus such as an inflatable sponge filled cuff 152. The inflatable sponge filled cuff 152 is generally toroid shaped when inflated and surrounds the sheath 122 adjacent its second end 128. The cuff 152 has an inflatable toroid shaped tube 154 made of an elastic material such as rubber or a like material. The toroid shaped tube 154 is affixed to the sheath 122 by conventional fastening techniques known in the art such as adhesives or vulcanization. The toroid shaped tube 154 defines an inner cavity which contains a flexible material such as sponge 156.

The inner cavity of the toroid shaped tube 154 is in fluid communication with a conventional source of vacuum such as a syringe (not shown) through the use of an air tube 158. The air tube 158 is located within the wall of the sheath 122 and extends along the length of the sheath 122 from the inner cavity of the toroid shaped tube 154 past the first end 126 of the sheath 122. The air tube 158 is connectable to the syringe (not shown) adjacent to the first end 126 of the sheath 122.

The inflatable sponge-filled cuff 152 is inflated in its natural state and generally toroid shaped (shown by phantom lines in FIG. 4). The inflated sponge filled cuff 152 generally has an outer diameter generally equal or greater than 2 centimeters. However, when vacuum is applied to the inner cavity of the toroid shaped tube 154 by the syringe (not shown), the inner cavity deflates and the sponge 156 is compressed within the inner cavity thereby minimizing the size of the sponge filled cuff 152. The reduced size of the sponge filled cuff 152 facilitates advancing the second end 128 of the sheath 122 through the upper alimentary canal.

When performing an endoscopy or other intubation of the upper alimentary canal using the endoscopic over-tube 120, a flexible lavage tube (not shown) is first advanced through the patient's upper alimentary canal and used to evacuate the stomach. The lavage tube (not shown) is extremely flexible and can be passed through the alimentary canal with minimal stimulation of the gag reflex. The sponge filled cuff 152 is then deflated by the vacuum source (not shown) to minimize the size of the cuff 152 during advancement of the sheath 122 into the alimentary canal. The second end 128 of the sheath 122 is then placed over the lavage tube (not shown) and advanced into the alimentary canal of the patient using the lavage tube (not shown) as an advancement guide. In the same manner as described with respect to the endoscopic over-tube 20, the sheath 122 is positioned within the upper alimentary canal such that the second end 128 of the sheath 122 is in the patient's esophagus, the stiffened region 142 is aligned with the patient's gag zone 33 (FIG. 2) and the mouthpiece 132 is retained within the patient's mouth.

The sponge filled cuff 152 is then inflated by disconnecting the syringe (not shown) from the air tube 158 thereby causing the inner cavity of the toroid shaped tube 154 to self-inflate through the expansion of the sponge 156. When the sponge filled cuff 152 inflates, it expands outward and presses against the wall of the esophagus thereby sealing the esophagus.

Once the esophagus is sealed, the lavage tube (not shown) is removed from the longitudinal bore 124 of the sheath 122 and a flexible endoscope (not shown) is advanced through the sheath 122 into the stomach and upper small intestine. The stiffened region 142 of the sheath 122 insulates the gag zone 33 from irritation caused by the flexible endoscope (not shown) as it is passed through the longitudinal bore 124 of the sheath 122. Because the esophagus is sealed, aspiration of stomach contents by the patient is prevented and the endoscopy may be completed without the threat of respiratory complication.

When the endoscopy is completed, the flexible endoscope (not shown) is removed from the longitudinal bore 124 of the sheath 122 and the sponge filled cuff 152 is deflated. The final step in the endoscopy is to remove the sheath 122 from the upper alimentary canal of the patient.

It is to be understood that even though numerous characteristics and advantages of the invention have been set forth in the forgoing description, together with details of the structure and function of the invention, the disclosure is illustrative only, and changes may be made in detail, especially in matters of shape, size and arrangement of the parts within the principles of the invention to the full extent indicated by the broad general meaning of the terms in which the appended claims are expressed.

What is claimed:

1. An endoscopic over-tube for receiving and guiding medical instrumentation into the upper alimentary canal of a patient comprising:

a) a bite block for insertion and retention in the mouth of the patient; and b) a flexible protective sheath engaging the bite block and adapted for insertion into the upper alimentary canal of the patient, the sheath having first and second ends and having a longitudinal bore, the sheath including a first end portion positioned proximate the first end a second end portion positioned proximate the second end, and an intermediate portion positioned between the first and second end portions, the intermediate portion including a stiffened region that is stiffer than the first and second end portions and is positioned a predetermined distance from the first end, such that when the sheath is inserted into the upper alimentary canal, the first end portion engages the bite block within the mouth of the patient, the second end portion is within the esophagus of the patient, and the stiffened region aligns substantially along the pharynx of the patient.

2. The endoscopic over-tube of claim 1, further comprising means for sealing the esophagus of the patient to protect the airway of the patient during endoscopy.

3. The endoscopic over-tube of claim 2, wherein the means for sealing includes an inflatable sponge-filled cuff surrounding the sheath adjacent the second end.

4. The endoscopic over-tube of claim 1, wherein the sheath has a tapered portion at the second end for assisting advancement of the sheath into the upper alimentary canal.

5. The endoscopic over-tube of claim 1, wherein the stiffened region comprises a thickened portion.

6. The endoscopic over-tube of claim 1, wherein the first end of the sheath is attached to the bite block.

7. The endoscopic over-tube of claim 1, wherein the intermediate portion has a circumference, and the stiffened region is generally coextensive with a portion of the circumference of the intermediate portion.

8. The endoscopic over-tube of claim 7, wherein the stiffened region is generally coextensive with substantially one half of the circumference of the intermediate portion.

9. An endoscopic over-tube comprising:

a) a bite block for insertion into the mouth of a patient; and b) a flexible protective sheath received by the bite block for insertion into the upper alimentary canal of the patient, the sheath having oppositely located first and second ends and defining a longitudinal bore for receiving medical instrumentation, the sheath including a first end portion positioned proximate the first end, a second end portion positioned proximate the second end, and an intermediate portion positioned between the first and second end portions, the intermediate portion including a thickened region that is stiffer than the first and second end portions, the thickened region being arranged and configured such that when the sheath is inserted into the upper alimentary canal, the thickened region is aligned substantially along the pharynx of the patient to prevent a gag reflex.

10. The endoscopic over-tube of claim 9, further comprising means for sealing the esophagus of the patient to protect the airway of the patient during endoscopy.

11. The endoscopic over-tube of claim 10, wherein the means for sealing includes an inflatable sponge-filled cuff surrounding the sheath adjacent the second end.

12. The endoscopic over-tube of claim 9, wherein the sheath has a tapered portion at the second end for assisting advancement of the sheath into the upper alimentary canal.

13. The endoscopic over-tube of claim 9, wherein the first end of the sheath is attached to the bite block.

14. A method for performing an endoscopy of the alimentary canal of a patient comprising:

a) providing a flexible protective sheath defining a longitudinal bore for receiving an endoscope, the sheath having a first end connected to a bite block and a second end adapted for insertion into the upper alimentary canal of the patient, the sheath further having a first end portion positioned proximate the first end, a second end portion positioned proximate the second end, and an intermediate portion positioned between the first and second end portions, the intermediate portion including a stiffened region that is stiffer than the first and second end portion;

b) inserting the second end of the sheath into the mouth of the patient;

c) advancing the second end of the sheath into the pharynx of the patient;

d) advancing the second end of the sheath into the esophagus of the patient such that the second end of the sheath is within the esophagus, the stiffened region is aligned with the pharynx of the patient and the bite block is within the mouth of the patient; and e) advancing an endoscope through the longitudinal bore of the sheath and into the alimentary canal of the patient, whereby the sheath prevents a gag reflex during endoscopy.

15. A method for performing an endoscopy of the alimentary canal of a patient comprising:

a) providing an endoscopic over-tube having a flexible protective sheath defining a longitudinal bore for receiving an endoscope, the sheath having a first end connected to a bite block and a second end adapted for insertion into the upper alimentary canal of the patient, the sheath including a first end portion positioned proximate the first end, a second end portion positioned proximate the second end, and an intermediate portion positioned between the first and second end portions, the intermediate portion including a stiffened region that is stiffer than the first and second end portions, the endoscopic over-tube further having sealing means surrounding the sheath adjacent the second end;

b) inserting the second end of the sheath into the mouth of the patient;

c) advancing the second end of the sheath into the pharynx of the patient;

d) advancing the second end of the sheath into the esophagus of the patient such that the second end of the sheath is within the esophagus, the stiffened region is aligned with the pharynx of the patient and the bite block is within the mouth of the patient;

e) inflating the sealing means to seal the esophagus of the patient thereby preventing damage to the patient's airway; and f) advancing an endoscope through the longitudinal bore of the sheath and into the alimentary canal of the patient, whereby the sheath prevents a gag reflex during endoscopy.

16. The method for performing an endoscopy of claim 15, further comprising using a lavage tube for guiding the sheath through the alimentary canal of the patient.

17. A method for performing an endoscopy of the alimentary canal of a patient comprising:

a) providing a flexible protective sheath defining a longitudinal bore for receiving an endoscope the sheath having a first end and a second end, the sheath further having a first end portion positioned proximate the first end, a second end portion positioned proximate the second end, and an intermediate portion positioned between the first and second end portions, the intermediate portion including a stiffened region that is stiffer than the first and second end portions;

b) inserting the second end of the sheath into the mouth of the patient;

c) advancing the second end of the sheath into the pharynx of the patient;

d) advancing the second end of the sheath into the esophagus of the patient such that the second end of the sheath is within the esophagus, the stiffened region is aligned with the pharynx of the patient and the first end is adjacent to the mouth of the patient; and e) advancing and endoscope through the longitudinal bore of the sheath and into the alimentary canal of the patient, whereby the sheath prevents a gag reflex during endoscopy.

18. A method for performing an endoscopy of the alimentary canal of a patient comprising:

a) providing an endoscopic over-tube having a flexible protective sheath defining a longitudinal bore for receiving an endoscope, the sheath having a first end and a second end and including a first end portion positioned proximate the first end, a second end portion positioned proximate the second end, and an intermediate portion positioned between the first and second end portions, the intermediate portion including a stiffened region that is stiffer than the first and second end portions, the endoscopic over-tube further having sealing means surrounding the sheath adjacent the second end;

b) inserting the second end of the sheath into the mouth of the patient;

c) advancing the second end of the sheath into the pharynx of the patient;

d) advancing the second end of the sheath into the esophagus of the patient such that the second end of the sheath is within the esophagus, the stiffened region is aligned with the pharynx of the patient and the first end is adjacent to the mouth of the patient;

e) inflating the sealing means to seal the esophagus of the patient thereby preventing damage to the patient's airway; and f) advancing an endoscope through the longitudinal bore of the sheath and into the alimentary canal of the patient, whereby the sheath prevents a gag reflex during endoscopy.

19. The method for performing an endoscopy of claim 13, further comprising using a lavage tube for guiding the sheath through the alimentary canal of the patient.

* * * * *

UNITED STATES PATENT AND TRADEMARK OFFICE
CERTIFICATE OF CORRECTION

PATENT NO. : 5,620,408

DATED : April 15, 1997

INVENTOR(S) : Vennes et al.

It is certified that error appears in the above-identified patent and that said Letters Patent is hereby corrected as shown below:

On the title page, item
[76], Inventors: "18905 12th Ave. North, Plymouth, Minn. 55447;" should read --8221 Amsden Rd., Bloomington, Minn. 55438--

Col. 4, line 47: "thickness stiffness" should read --thickness/stiffness--

Col. 8, line 47, claim 14: "portion" should read --portions--

Signed and Sealed this

Ninth Day of December, 1997

*Attest:*

BRUCE LEHMAN

*Attesting Officer*   Commissioner of Patents and Trademarks